United States Patent [19]

Kerkenaar et al.

[11] Patent Number: 5,182,194

[45] Date of Patent: Jan. 26, 1993

[54] METHOD FOR PREPARING P-MENTHA-8-THIOL-3-ONE

[75] Inventors: Antonius Kerkenaar, Blaricum; Diederik J. M. Schmedding, Driebergen; Jan Berg, Nieuwegein, all of Netherlands

[73] Assignee: Nederlandse Organisatie Voor Toegepast-Natuurwetenschappe Lijk Onderzoektno, The Hague, Netherlands

[21] Appl. No.: 148,418

[22] Filed: Jan. 26, 1988

[30] Foreign Application Priority Data

Jan. 30, 1987 [NL] Netherlands ........................ 8700240

[51] Int. Cl.$^5$ ..................... C12P 11/00; C12P 7/26; C12N 9/88; C07C 319/02
[52] U.S. Cl. ..................... 435/130; 435/148; 435/232; 568/64; 562/507
[58] Field of Search ............... 435/282, 232, 130, 260, 435/148, 280, 188; 568/354.64; 562/507

[56] References Cited

U.S. PATENT DOCUMENTS 4,032,478  6/1977  Lamparsky et al. ............ 512/7
4,034,044  7/1977  Sundt et al. .................... 426/535
4,328,311  5/1982  Rowley et al. .................. 435/188

FOREIGN PATENT DOCUMENTS 974250  9/1975  Canada ........................... 167/321
991084  6/1976  Canada ........................... 167/321
999603  11/1976  Canada .......................... 167/321

OTHER PUBLICATIONS

Bakke et al, Trends in Biochemical Sciences, Dec. 1984, pp. 517-521.
The Journal of Biological Chemistry, vol. 253, No. 24 issued Dec. 25, 1978, pp. 8854-8859.
Edwards and Owen, "Planta", (1986), vol. 169 pp. 208-215.
Salques, Cheynier, Gunata and Wylde, Journal of Food Science, vol. 51, No. 5, 1985 pp. 1191-1194.
Kitazume, Ikeya and Murata, J. Chem. Soc., Chem. Commun., 1986, pp. 1331-1333.
Ito and Fujita, Biochimica et Biophysica Acta, vol. 672, (1981), pp. 151-157.
Glass and Burley, Applied and Environmental Microbiology, May 1985, pp. 1146-1153.
Lamoureux and Rusness, Pesticide Biochemistry and Physiology, vol. 14, (1980), pp. 50-61.
Pilnik and Rombouts, Carbohydrate Research, vol. 142 (1985), pp. 93-105.
Glass, T. L., et al., "Biotransformation of 16α-hydroxyprogesterone by Eubacterium sp. 144: non-enzymatic addition of L-cysteine to $^{16}$-progesterone", *J. Lipid Res.* (1982), vol. 23, pp. 352-356.
Larsen et al., "Cysteine Conjugate Beta Lyase . . . " *Mol. Pharmacol.* 29 (1) 1986 pp. 97-103.
Larsen et al. "Cysteine Conjugate Beta Lyase . . . " *Xenobiotica* 13 (11) 1983 pp. 689-700.

*Primary Examiner*—Irene Marx
*Attorney, Agent, or Firm*—Beveridge, DeGrandi & Weilacher

[57] ABSTRACT

Method for preparing thiol compounds by coupling cysteine having the formula HS—CH$_2$—CH(NH$_2$)COOH via and —S— bridge to a hydrocarbon compound and subsequently reacting the cysteine conjugate obtained with β-lyase to form the relevant thiol compounds. For instance it is possible to prepare the flavor p-mentha-8-thiol-3-one starting from pulegone as illustrated in the diagram below:

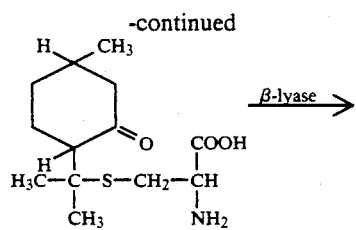
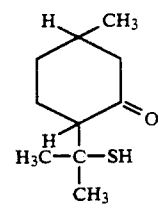
2 Claims, 3 Drawing Sheets

METHOD FOR PREPARING P-MENTHA-8-THIOL-3-ONE

The invention relates to a method for preparing thiol compounds.

In Pesticide Biochemistry and Physiology 14, pages 50-61 (1980), the in vitro metabolism of pentachloronitrobenzene (PCNB) into pentachloromethylthiobenzene (PCTA) by means of an enzyme system obtained from onions is described. More particularly, this reference relates to the in vitro preparation of PCTA from PCNB at a pH of 7.9 by means of an enzyme system which contains dithiothreitol, glutathione and S-adenosylmethionine. Said enzyme system was prepared from onion roots by ammonium sulphate fractionation and differential centrifugation. The enzyme system contained glutathione-S transferase activity with PCNB, C-S-lyase activity (also termed β-lyase activity) with S-(pentachlorophenyl)cysteine, S-adenosylmethionine-methyl transferase activity with pentachlorothiophenol (PCTP) and probably a few other peptidase activities. The yield of the thiol compound concerned, namely pentachlorothiophenol (PCTP) is, however, negligible in this known method compared with the yield of PCTA (see page 55, right-hand column, lines 10-13 from bottom) so that this method is considered unsuitable for preparing thiol compounds.

In Journal of Biological Chemistry, vol. 253, 24, pages 8854-8859 (1978), the cysteine conjugate β-lyase in rat liver is described. This enzyme catalysing cleavage of the thioether linkage in cysteine conjugates has been purified about 500-fold from rat liver cytosol. However, according to the Chapter "Assay Methods" (page 8855) the obtained thiol compounds were directly methylated whereafter the methylated derivatives were identified by spectroscopy methods.

A method defined in the introduction has now been found which is characterized in that cysteine is coupled via an —S— bridge to a hydrocarbon compound and subsequently the cysteine conjugate obtained is reacted with a β-lyase to form the thiol compound(s) concerned and also $NH_3$ en $CH_3$—CO—COOH.

From the above it may be inferred that the method according to the invention can be subdivided into two steps:

a) the preparation of the cysteine conjugate; and
b) the splitting of said cysteine conjugate into, inter alia, the thiol compound(s) concerned.

The preparation of the cysteine conjugate may be carried out, for example, by an addition or substitution reaction. More particularly, the addition reaction of cysteine can be carried out with a compound having the formula $(R_1)(R_2)C=C(R_3)$—CO—$R_4$ in which the symbols $R_1$-$R_4$ represent a hydrogen atom or an optionally saturated and/or heterogeneous hydrocarbon group or, together with the carbon atom to which the symbols are bonded, form one or two, optionally saturated and/or heterogeneous ring systems. For example, the symbols $R_1$-$_4$ represent a hydrogen atom, an alkyl group containing 1-5 carbon atoms, an alkenylene group containing 2-5 carbon atoms, a cycloalkyl or cycloalkenyl group containing 5-10 carbon atoms or an aryl group containing 6-10 carbon atoms, which abovementioned groups may be substituted by halogen atoms and/or one or more groups containing carbon, nitrogen, sulphur, oxygen and/or halogen atoms. Preferably, the symbols $R_2$ and $R_3$ represent a hydrogen atom or an alkyl group containing 1-3 carbon atoms and $R_4$ an optionally heterogeneous hydrocarbon group bonded via an —O— bridge.

For example, unsaturated sugars having the formula

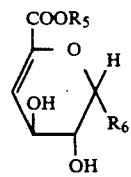

which the symbol $R_5$ represents a hydrogen atom, an alkyl group containing 1-24 carbon atoms or an alkaline ion and $R_6$ represents a group consisting of 1-7 monosaccharides selected from the group consisting of glucose, mannose, galactose, arabinose, fucose, xylose, rhamnose, uronic acids and derivatives thereof like the acetates, pyruvates, amines and sulphates are also suitable as starting material for the addition reaction of cysteine. Preferably $R_6$ represents a glucose-rhamnose-glucose group. The obtained cysteine-conjugates are simply convertable to compounds with the formula

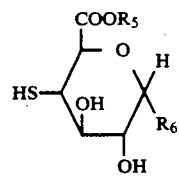

having flavouring properties.

The above addition reactions can be carried out in a purely chemical manner but also in a biochemical manner under the influence of an enzyme such as esterase or lipase.

The preparation of a cysteine conjugate by means of a substitution reaction can be carried out by means of nucleophilic substitution of glutathione in the presence of glutathione transferase, it being possible for Cl, $NO_2$ and H to appear as the group to be replaced. The glutathione conjugate is converted enzymatically into the cysteine conjugate (the glutathione conjugate is converted by means of a carboxy peptidase into the γ-glutamylcysteine conjugate which is in turn converted into the cysteine conjugate under the influence of γ-glutamyl transpeptidase). However, such a synthesis route is not as yet being used advantageously owing to the additional processing steps.

Many types of cysteine conjugates are known as such from the prior art. For example, the preparation of such cysteine conjugate is known from Applied and Environmental Microbiology, May 1985, pages 1146-1153. In this reference, 16-dehydroprogesterone, in particular, is converted with L-cysteine in a non-enzymatic manner into 16-S-cysteinylprogesterone. Said cysteinyl compound can be converted in the presence of β-lyase into 16-mercaptoprogesterone by means of the second stage of the method according to the invention. The diagram below illustrates the synthesis route described above:

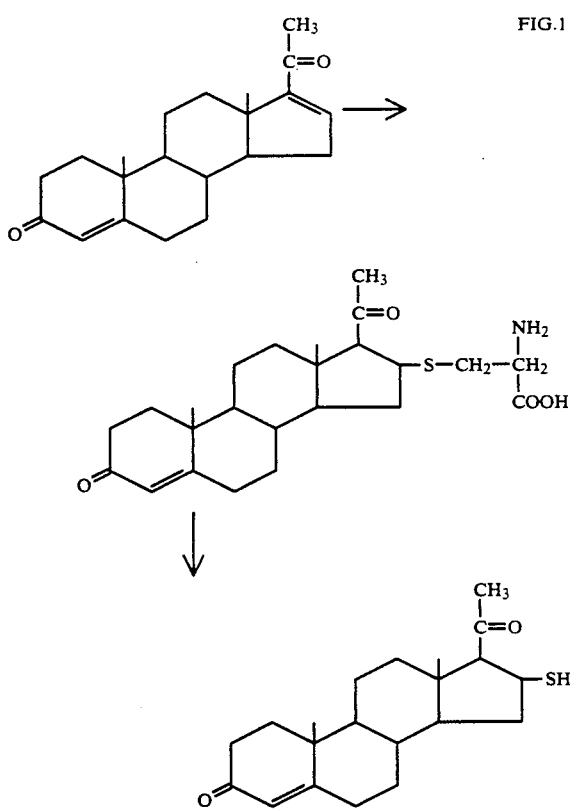

FIG.1

The thiolsteroid shown above has specific pharmacological properties.

The formation of cysteine conjugates of 3-(3,4-dihydroxyphenyl)analine is reported in Biochimica et Biophysica Acta 672 (1981), pages 151–157. As indicated on page 155 of this reference, polyconjugates can also be obtained in addition to some monoconjugates. These singly or multiply conjugated compounds can also be converted by means of the β-lyase to be used according to the invention into the corresponding mono- or polythiol derivatives.

Reference may be made to the following additional references relating to specific cysteine conjugates or derivatives derived therefrom:
1) J.Chem.Soc.Chem.Commun. 1986, pages 1331–1333;
2) Journal of Food Science, vol. 51, no. 5, 1986, pages 1191–1194;
3) Planta (1986) 169: 208–215; and
4) Carbohydrate Research 142 (1985), pages 93–105.

The cysteine used in the method according to the invention has the formula HS—CH$_2$—CH(NH$_2$)—COOH. In view of the spectrum of activity of the β-lyase to be used in the method according to the invention, L-cysteine is used.

The β-lyase (also termed C-S-lyase or cysteine conjugate β-lyase) to be used in the method according to the invention is an enzyme dependent on a pyridoxal 5-phosphate (vitamin B6). In addition to being present in a large number of intestinal bacteria (in 24 out of the 43 intestinal bacteria investigated), the β-lyase is also present in some vegetable and animal cells (Larsen G. L., "Distribution of cysteine conjugate β-lyase in gastrointestinal bacteria and the environment, Xenobiotica 15, 199–209 (1985)). The bacterial β-lyases are able to convert a wide spectrum of substrates, in particular both S-alkyl- and S-arylcysteine conjugates, whereas the spectrum of activity of β-lyases of vegetable or animal origin is limited. Measured with the cysteine-propachlor conjugate (an S-alkylcysteine conjugate), the β-lyase originating from the anaerobic intestinal bacterium Eubacterium limosum is the most active enzyme and has the lowest substrate specificity (Larsen, loc. cit.). If, however, the conversion of S-(2-benzothiazolyl)cysteine (an S-arylcysteine conjugate) is examined, it emerges that the β-lyase from an anaerobic Fusobacterium species has virtually an identical activity. β-lyase from F.necrophorum and E. limosum differ not only in substrate specificity, but also in size, namely 228 kd and 75 kd (2x38 kd) and alaso in stability. The enzyme from F.necrophorum requires pyridoxal 5-phosphate for stability but is then also more stable to heat. β-lyases from E.limosum and F.varium exhibit no activity with D-cysteine conjugates and have, in general, a lower activity for S-alkylcysteine conjugates than for S-arylcysteine conjugates. Eubacterium limosum ATCC 10825, Fusobacterium necrophorum ATCC 25286 and Fusobacterium varium ATCC 8501 are available from American Type Culture Collection, 12301 Parklawn Drive, Rockville, Md. 20852.

The isolation of β-lyase from both E.limosum and F.varium does not have to be carried out under anaerobic conditions. This indicates that the enzyme is not sensitive to oxygen. It also emerges from the isolation method that the enzyme is located in the cell. The second step described above of the method according to the invention can therefore be carried out with purified-/extracted β-lyase or, if the substrates are absorbed by the bacterial cells and are converted therein, with the respective bacteria themselves.

The method according to the invention results in many types of thiol compounds with divergent applications. Examples of substances to be prepared pertain to the field of perfumes and flavourings (p-mentha-8-thiol-3-one, damascone derivative), pharmacological steroid compounds and repellants (Warburganal).

The invention further relates to the purification or separation of α,β-unsaturated and also saturated aldehydes and ketones from, in particular, complex vegetable products using the cysteine conjugates derived therefrom and also to the enrichment associated therewith of the residual substances also present in said products. After separation from the original product by means of, for example, steam distillation, the cysteine conjugates formed are split into the purified aldehyde or ketone and the cysteine. This recovered cysteine an subsequently be employed again in the cysteine conjugate preparation.

The formation of the cysteine conjugate (II) is shown on the basis of the diagram below for α,β-unsaturated aldehydes and ketones (I) having the formula (R$_1$)(R$_2$)—C═C(R$_3$)—(O—R$_4$) in which R$_1$-R$_4$ have the meaning stated above; this conjugate formation is often followed by the attachment of a cysteine molecule to the carbonyl group of the aldehyde or ketone to form a thiazolidine-4-carboxylic acid derivative (III).

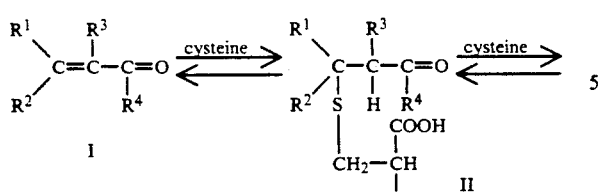

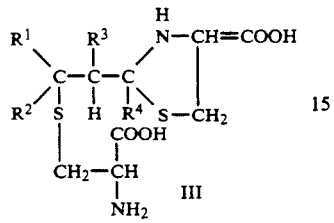

As examples of such α,β-unsaturated aldehydes and ketones, mention may be made of:

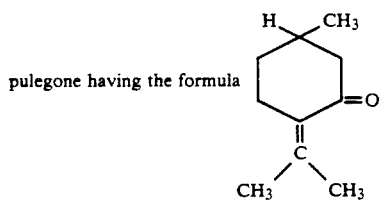

pulegone having the formula

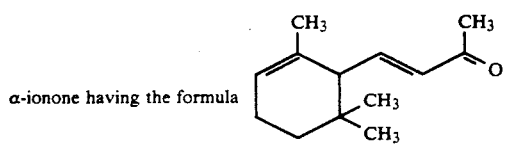

α-ionone having the formula

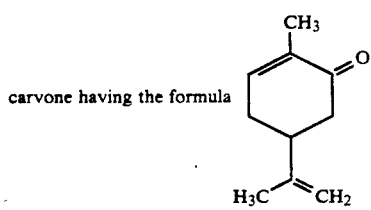

carvone having the formula and citral having the formula $(CH_3)_2C=CH-CH_2-CH_2-(CH_3)C=CH-CHO$.

For saturated aldehydes and ketones having the formula $(R_1)(R_2)C=O$ in which $R_1$ and $R_2$ have the above-mentioned meaning, the formation of the thiazolidine-4-carboxylic acid derivatives derived therefrom may be represented as follows.

As examples of such saturated aldehydes and ketones mention may be made of:

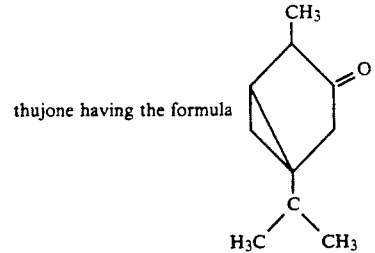

thujone having the formula and

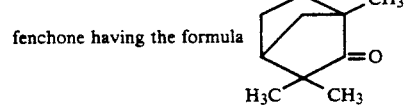

fenchone having the formula

An important advantage of the purification described above lies in the fact that no biologically foreign reagents such as bisulphite (not usable in the case of α,β-unsaturated carbonyl compounds), hydroxylamine, 1-naphthylamine-5-sulphonic acid, hydrazine, thiosemicarbazide etc have to be used. The purification can also be carried out under mild conditions as regards pH and temperature and the cysteine is recovered.

The invention is explained on the basis of the examples below, Examples I and II relating to the thiol preparation and Example III relating to the purification method; these examples should not be interpreted as restrictive.

EXAMPLE I

Figure 1:
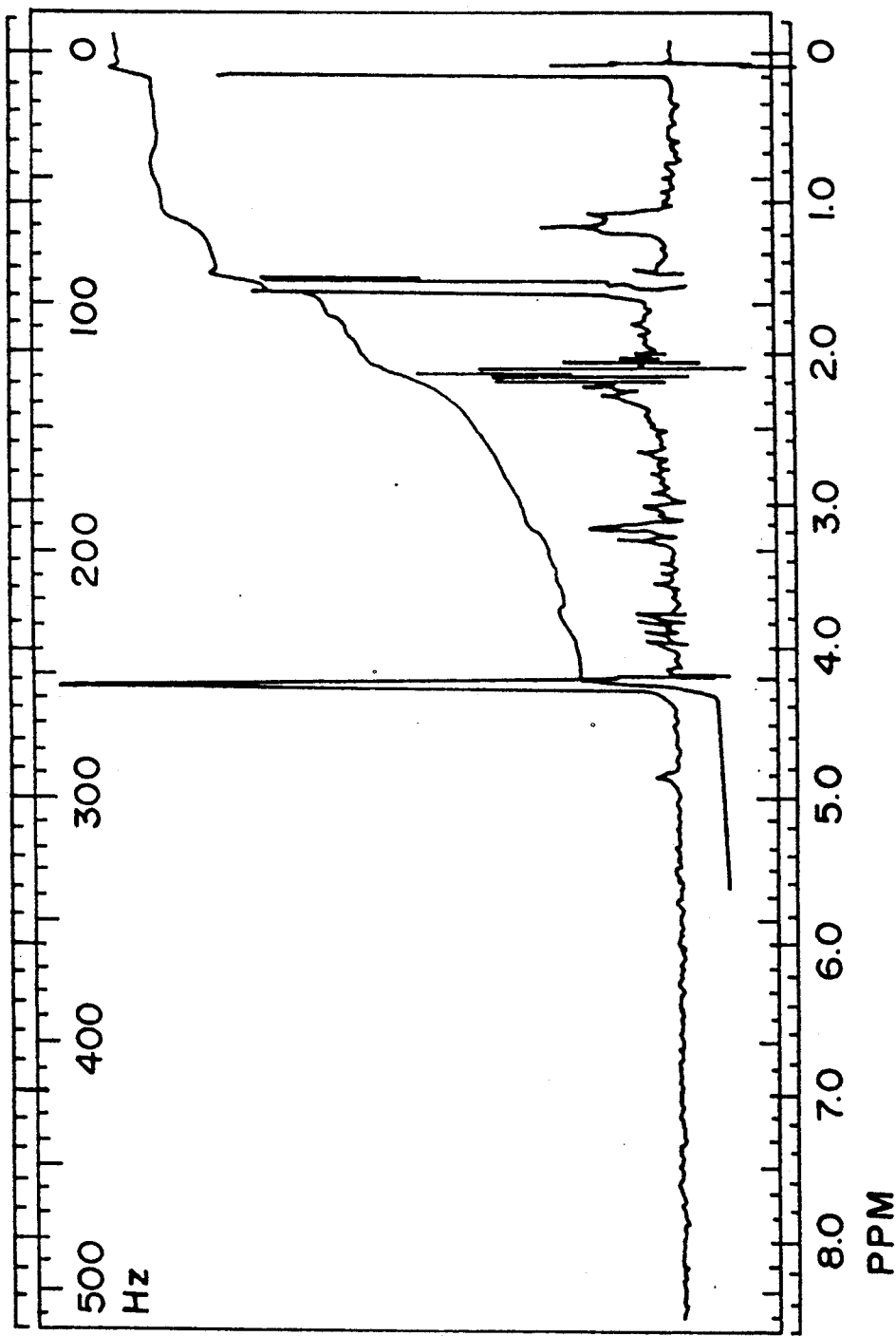
FIG. 1 shows the 90 MHz H-NMR spectrum of the product obtained in example 1.
Figure 2A:
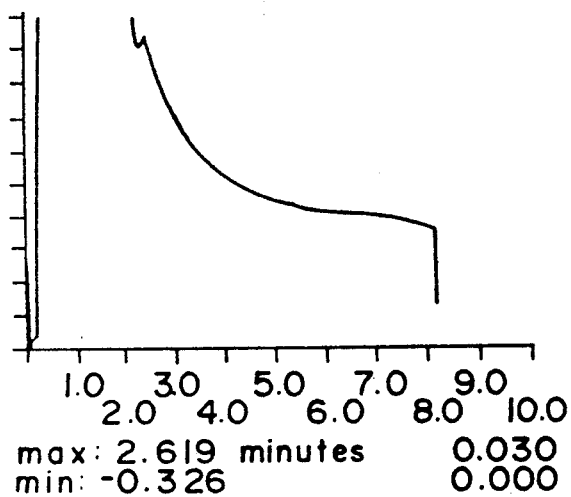
FIGS. 2a-2c show gas chromatography analysis of the samples of example 1.
Figure 2B:
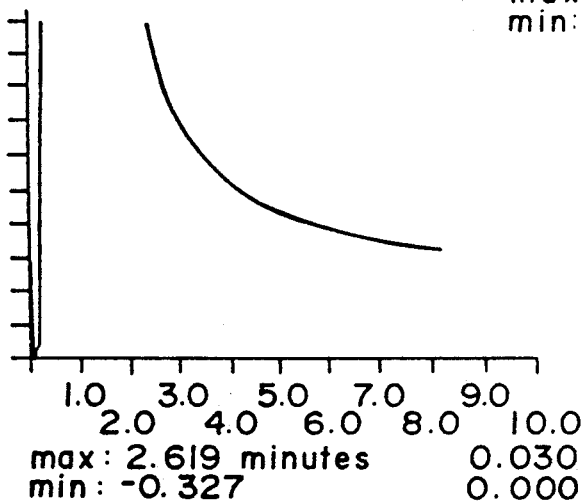
Figure 2C:
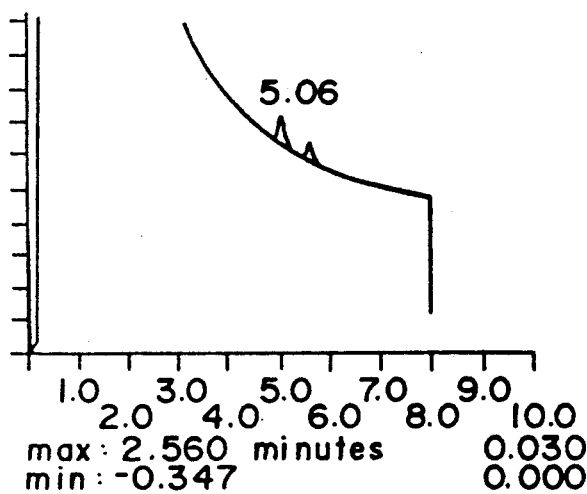

In this example, the starting point is pulegone, which is converted via S-cysteinyl— pulegone into p-mentha-8-thiol-3-one. This preparation is illustrated in the diagram below.

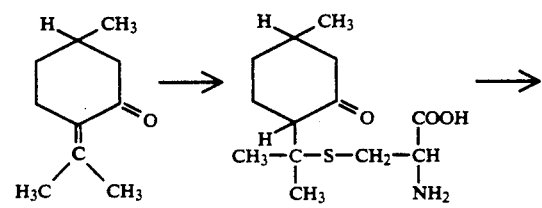

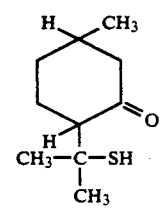

Stage 1) Preparation of S-cysteinyl— pulegone 12.2 g of L-cysteine (0.1 mol) (high purity analytical grade supplied by Fluka A. G.), 16.3 ml of pulegone (0.1 mol) and 2.0 g of $KHCO_3$ (0.02 mol) were stirred for 22 hours in 100 ml of $H_2O$ at room temperature. The yoghurt-like mixture, which was no longer stirrable, was then allowed to stand for 3 days. The product obtained was then filtered off by suction and washed respectively with 100 and 2×50 ml of $H_2O$. After drying over $CaCl_2$ in vacuo, the product was washed with acetone. The yield was 17.9 g. Appendix 1 shows the 90 MHz H-NMR spectrum of the product obtained.

More particularly, an elementary analysis of the product purified by thin-layer chromatography clearly indicates a 1:1 reaction product.

| Elementary analysis (carried out in duplicate) | |
| --- | --- |
| Found: | Calculated (substance + ½ mol of $H_2O$): |
| %C: 54.76 | 55.29 |
| %H: 8.36 | 8.57 |
| %N: 5.01 | 4.96 |
| %O: 19.60 | 19.83 |
| %S: 11.13 | 11.35 |

Stage 2) Splitting of the S-cysteinyl— pulegone

The organism used in this stage is *Eubacterium limosum* having the ATCC no. 10825. Said organism was cultured under anaerobic conditions at 37° C. on a P-medium which had the composition below:

| Composition of P-medium: | | |
| --- | --- | --- |
| Casein peptone | (Difco) | 10 g/l |
| Beef extract | (Difco) | 3 g/l |
| Yeast extract | (Difco) | 3 g/l |
| Glucose | (Merck) | 2 g/l |
| Tween 80 | (Serva) | 1 g/l |
| Cysteine-HCl | (Fluka) | 0.5 g/l |
| Resazurin | (Serva) | 0.25 g/l |
| Salt solution | (analytical grade) | 40 ml/l |
| Final pH: 7.2 | | |
| The salt solution consisted of: | | |
| $CaCl_2$ | | 0.2 g/l |
| $MgSO_4.7H_2O$ | | 0.2 g/l |
| $K_2HPO_4$ | | 1.0 g/l |
| $KH_2PO_4$ | | 1.0 g/l |
| $NaHCO_3$ | | 10.0 g/l |
| NaCl | | 2.0 g/l |

The cell material for producing β-lyase as obtained by culturing *E.limosum* (3% inoculation) on the abovementioned P-medium in serum bottles having a capacity of 300 ml. By filling the bottle with P-medium to a few centimeters below the rim, the medium became sufficiently low in oxygen as a result of sterilization to make growth of *E.limosum* possible. After an incubation time of 1 day at 37° C., the cells were harvested by centrifuging them at 50,000×g for 20 minutes. The cells were subsequently washed twice with a buffer having a pH of 7 which contained 50 mM of phosphate and 50 mM of pyridoxal-HCl. The pellet (approx. 1 g wet weight from 300 ml) was taken up in 10 ml of buffer.

S-cysteinyl— pulegone (0.3 g/l=1.1 mM) was converted in the buffer with the concentrated cell suspension of *E.limosum* described above (final concentration: 1.6 mg dry weight/ml). The reaction was carried out for 1 hour at 30° C. and was terminated by centrifuging the reaction mixture for 5 minutes at 11,000×g.

As a control, two tests were carried out:

a) As a control, boiled cells (denatured enzymes) were used in the test described above.

b) In order to be able to assess whether the SH product (p-mentha-8-thiol-3-one) had converted by the S-methyl transferase into the S-methyl product (p-mentha-8-thiomethyl-3-one), the cells were also incubated with p-mentha-8-thiol-3-one.

The results of gas chromatography analysis of this example (samples no. 1) and the two control tests (samples 2 and 3) are shown in Appendix 2.

To carry out the abovementioned gas chromatographic analysis, 1 part of chloroform ($CHCl_3$) was mixed with 1 part of the reaction mixture obtained. 1 μl of this extract was injected into a gas chromatograph having a 20 M carbowax column, (1.3 m RVS, column temperature: 145° C., injection port and TCD temperature: 160° C.).

EXAMPLE II

The method according to Example I was repeated, but with the difference that, instead of being carried out on a 1 ml scale, the test was carried out on a 10 ml scale. In this test, the cells were used in a double concentration, viz. 3.2 mg dry weight/ml and the incubation was carried out for 3 hours at 37° C. For a gas chromatographic analysis, a sample (sample B) was taken from this in the following manner.

One part of dichloromethane ($CH_2Cl_2$) was mixed with 4 parts of the reaction mixture. 0.4 μl of this extract was injected into a Varian gas chromatograph in which a 10 % FFAP-chromosorb was provided in a WAW column (2m RVS, i.d. 1/8") (column temperature: 160° C.; injection port and FID temperature: 180° C.).

As a comparison, in addition to the gas chromatogram of sample B shown in Appendix 3 as a control, the gas chromatograms of a) p-mentha-8-thiol-3-one, b) p-mentha-8-thiomethyl-3-one, c) pulegone, and d) S-cysteinylpulegone were recorded without cells being used at the same time.

Figure 3A:
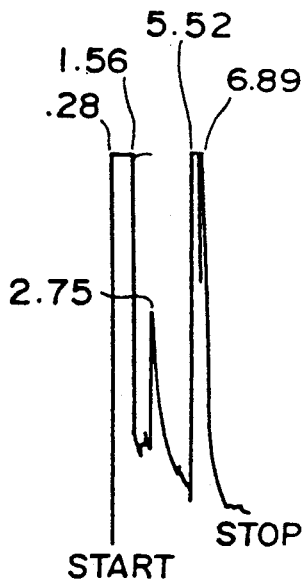
FIGS. 3a-3c show gas chromatography analysis of some extracts of example 2.
Figure 3B:
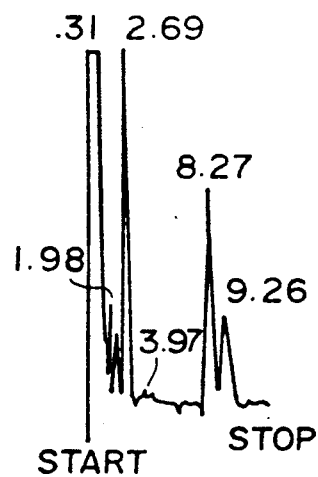
Figure 3C:
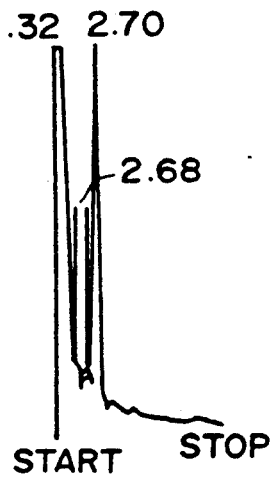
Figure 3D:
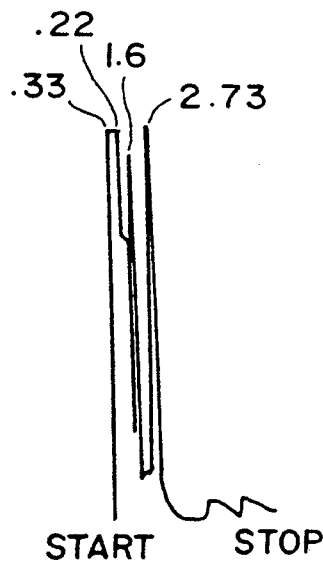
Figure 3E:
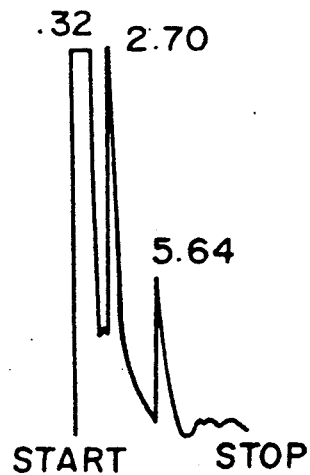

It follows from the chromatograms shown in Appendix 3, inter alia, that no detectable p-mentha-8-thiomethyl-3-one is formed (compare 3b with 3e). The pulegone peak in FIGS. 3d and 3e (retention time 2.7 min.) may be explained by the fact that some of the S-cysteinyl— pulegone dissolves in the extraction agent and is decomposed in the gas chromatograph (160° C.).

The chromatogram of chemically synthesized p-mentha-8-thiol-3-one (FIG. 3a) reveals an isomer ratio of approximately 2:1. The biologically prepared p-mentha-8-thiol-3-one (FIG. 3e) has a completely different ratio of the two isomers which is approximately 9:1.

EXAMPLE III

As the starting product, a pulegone product of vegetable origin having a pulegone content determined by gas chromatography of 87.7 % by weight was used. As impurities in such a product, mention is made, inter alia, of -L-menthone having the formula

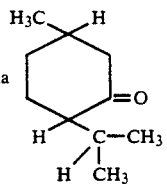

and

-isopulegone having the formula

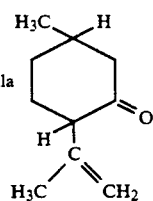

which cannot be separated or can virtually not be separated from pulegone, for example, by means of fractional distillation.

2,5 g of S-cysteinyl-pulegone.½ H₂O was prepared in accordance with the manner stated in stage (1) of Example I. This product was subjected to a steam distillation until no further pulegone distilled over. Subsequently, the distillate was extracted with carbon tetrachloride, after which the extract obtained, after drying over sodium sulphate, was evaporated down under vacuum. The yield was 1.3 g of pulegone (96.4 % of the theoretical quantity) which had a purity of 97.9 % as determined by gas chromatography.

EXAMPLE IV

A commercial cocoa mix is used to prepare two different batches of beverage. The first batch is evaluated without any further addition while p-mentha-8-thiol-3-one prepared according to Example 11 is added to the second batch in the ratio of 20 /µg of said p-mentha-8-thiol-3-one to each kilo of cocoa beverage. The beverage containing p-mentha-8-thiol-3-one has a fuller and richer flavour comparing to the beverage without p-mentha-8-thiol-3-one.

We claim:

1. A method for preparing thiol compounds comprising reacting cysteine non-enzymatically with pulegone to form a cysteine conjugate compound, subsequently reacting the cysteine conjugate so obtained with β-lyase selected from the group consisting of *Eubacterium limosum*, *Fusobacterium necrophorum* and *Fusobacterium varium* β-lyases to form p-mentha-8-thiol-3-one and recovering said p-mentha-8-thiol-3-one.

2. A method for preparing thiol compounds comprising reacting cysteine non-enzymatically with pulegone to form a cysteine conjugate compound, subsequently reacting the cysteine conjugate so obtained with *Eubacterium limosum* β-lyase to form p-mentha-8-thiol-3-one.

* * * * *

UNITED STATES PATENT AND TRADEMARK OFFICE
CERTIFICATE OF CORRECTION

PATENT NO. : 5,182,194
DATED : January 26, 1993
INVENTOR(S) : Antonius Kerkenaar, Diederik J.M. Schmedding, Jan Bert It is certified that error appears in the above-indentified patent and that said Letters Patent is hereby corrected as shown below:

At the end of claim 2, please insert the following phrase --and recovering said p-mentha-8-thiol-3-one--.

Signed and Sealed this

Twenty-ninth Day of March, 1994

Attest:

BRUCE LEHMAN

Attesting Officer     Commissioner of Patents and Trademarks